United States Patent
Pu et al.

(10) Patent No.: US 8,809,815 B2
(45) Date of Patent: Aug. 19, 2014

(54) PARTICLE-BEAM ENERGY CHANGING APPARATUS, PARTICLE BEAM THERAPY SYSTEM INCLUDING THE SAME, AND METHOD OF CHANGING PARTICLE BEAM ENERGY

(75) Inventors: Yuehu Pu, Tokyo (JP); Taizo Honda, Tokyo (JP); Takaaki Iwata, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/985,759

(22) PCT Filed: Apr. 25, 2011

(86) PCT No.: PCT/JP2011/060057
§ 371 (c)(1),
(2), (4) Date: Aug. 15, 2013

(87) PCT Pub. No.: WO2012/147149
PCT Pub. Date: Nov. 1, 2012

(65) Prior Publication Data
US 2013/0320245 A1    Dec. 5, 2013

(51) Int. Cl.
*A61N 5/10* (2006.01)
*G21K 1/10* (2006.01)

(52) U.S. Cl.
CPC ....... *A61N 5/1048* (2013.01); *A61N 2005/1087* (2013.01); *A61N 5/1042* (2013.01); *G21K 1/10* (2013.01); *A61N 2005/1095* (2013.01)
USPC .................................................. 250/492.3

(58) Field of Classification Search
CPC ............................................. A61N 2005/1087
USPC ........................................... 250/492.3, 503.1
See application file for complete search history.

(56) References Cited

U.S. PATENT DOCUMENTS

| 6,034,377 A | 3/2000 | Pu |
| 6,891,177 B1 | 5/2005 | Kraft et al. |

(Continued)

FOREIGN PATENT DOCUMENTS

| JP | 11-408 A | 1/1999 |
| JP | 11-142600 A | 5/1999 |

(Continued)

OTHER PUBLICATIONS

International Search Report (PCT/ISA/210) issued on May 24, 2011, by the Japanese Patent Office as the International Searching Authority for International Application No. PCT/JP2011/060057.

*Primary Examiner* — Nicole Ippolito
*Assistant Examiner* — Eliza Osenbaugh-Stewar
(74) *Attorney, Agent, or Firm* — Buchanan Ingersoll & Rooney PC

(57) ABSTRACT

There is provided a particle-beam energy changing apparatus that is capable of changing energy of a particle beam quickly and silently, in which a first energy changing unit and a second energy changing unit for changing energy of a particle beam passing therethrough by varying thicknesses of their attenuators attenuating the particle beam energy are arranged so that the particle beam passes through the first energy changing unit and the second energy changing unit; and the maximum attenuation amount by the first energy changing unit is set smaller than the maximum attenuation amount by the second energy changing unit.

6 Claims, 9 Drawing Sheets

(56) References Cited

U.S. PATENT DOCUMENTS

| | | | |
|---|---|---|---|
| 8,030,627 B2 * | 10/2011 | Gentry et al. | 250/492.3 |
| 8,049,187 B2 * | 11/2011 | Tachikawa | 250/492.1 |
| 8,193,520 B2 * | 6/2012 | Pu | 250/505.1 |
| 8,575,564 B2 * | 11/2013 | Iwata | 250/396 R |

FOREIGN PATENT DOCUMENTS

| | | |
|---|---|---|
| JP | 2003-320039 A | 11/2003 |
| JP | 4490198 B2 | 4/2010 |
| WO | WO 00/49624 A1 | 8/2000 |

* cited by examiner

PARTICLE-BEAM ENERGY CHANGING APPARATUS, PARTICLE BEAM THERAPY SYSTEM INCLUDING THE SAME, AND METHOD OF CHANGING PARTICLE BEAM ENERGY

TECHNICAL FIELD

The present invention relates to a particle-beam energy changing apparatus that is used such as for irradiating with a particle beam a diseased site in accordance with its three-dimensional shape. The apparatus is included in a particle beam therapy system that performs therapy by irradiating a diseased site such as a tumor with a particle beam.

BACKGROUND ART

In a particle beam therapy, a high-energy particle beam, such as a proton beam or a carbon beam accelerated up to 70% of the light velocity, is utilized. These high-energy particle beams have the following features when irradiated into a body. Firstly, almost all of irradiated particle beams stop at a depth position proportional to the particle beam energy raised to the 1.7th power. Secondly, the energy density (referred to as a dose), which is imparted to the irradiation path through which the particle beam passes until it stops in a body, becomes maximum at the particle-beam stop position. A distinctive deep dose distribution curve formed along a path through which a particle beam passes is referred to as "Bragg curve". The position where the dose value becomes maximum is referred to as "Bragg peak".

A three-dimensional particle beam irradiation system is contrived in such a way that, while it scans the Bragg peak position in accordance with the three-dimensional shape of a tumor and adjusts the peak dose at each scanning position, a predetermined three-dimensional dose distribution is formed in a tumor region, which is a target preliminarily determined by an imaging diagnosis. The scanning of the position where a particle beam stops includes scanning in transverse directions (X and Y directions) which are approximately perpendicular to the irradiation direction of a particle beam and scanning in a depth direction (Z direction) which is the irradiation direction of a particle beam. In the transverse-direction scanning, there exists a method of moving a patient with respect to a particle beam and a method of moving the position of a particle beam by use of an electromagnet or the like; in general, the method utilizing an electromagnet is adopted. Scanning in the depth direction is performed only by changing the energy of a particle beam. There are two methods for changing particle beam energy. One method uses an accelerator for changing energy; and the other method uses an energy changing apparatus called a range shifter (including an apparatus referred to as "energy selection system" serving as an energy changing and analyzing unit) installed in a beam transport system or an irradiation system. A commonly employed method is a method that uses a range shifter (for example, Patent Document 1 and Patent Document 2).

PRIOR ART DOCUMENT

Patent Document

Patent Document 1: JP H11-000408 A
Patent Document 2: WO00/49624 A

SUMMARY OF THE INVENTION

Problem that the Invention is to Solve

In a particle-beam energy changing apparatus, i.e., a range shifter that is disclosed in FIG. 1A or 1B of Patent Document 1 or in FIG. 5 or 6 of Patent Document 2, in order to change the energy by energy attenuation when an irradiation requires a large amount of energy variation, a range shifter member necessarily increases in thickness. Consequently, the mass of the range shifter member actuated in and out increases, which arises problems of difficulty in quick energy change as well as increase in vibration and noise when actuating. The present invention is made to resolve such problems with a conventional particle-beam energy changing apparatus, and to provide a particle-beam energy changing apparatus that is capable of quick operation with low noise.

Means for Solving the Problem

In a particle-beam energy changing apparatus according to the present invention, a first energy changing unit and a second energy changing unit for changing energy of a particle beam passing therethrough by varying thicknesses of their attenuators attenuating the particle beam energy are arranged so that the particle beam passes through the first energy changing unit and the second energy changing unit, and a maximum attenuation amount by the first energy changing unit is set smaller than a maximum attenuation amount by the second energy changing unit.

Advantages of the Invention

A particle-beam energy changing apparatus according to the present invention is capable of changing particle beam energy quickly and with low noise, and when applied to a particle beam therapy system, the apparatus can shorten the total irradiation time in a therapy.

EMBODIMENTS FOR CARRYING OUT THE INVENTION

Embodiment 1

Figure 1:
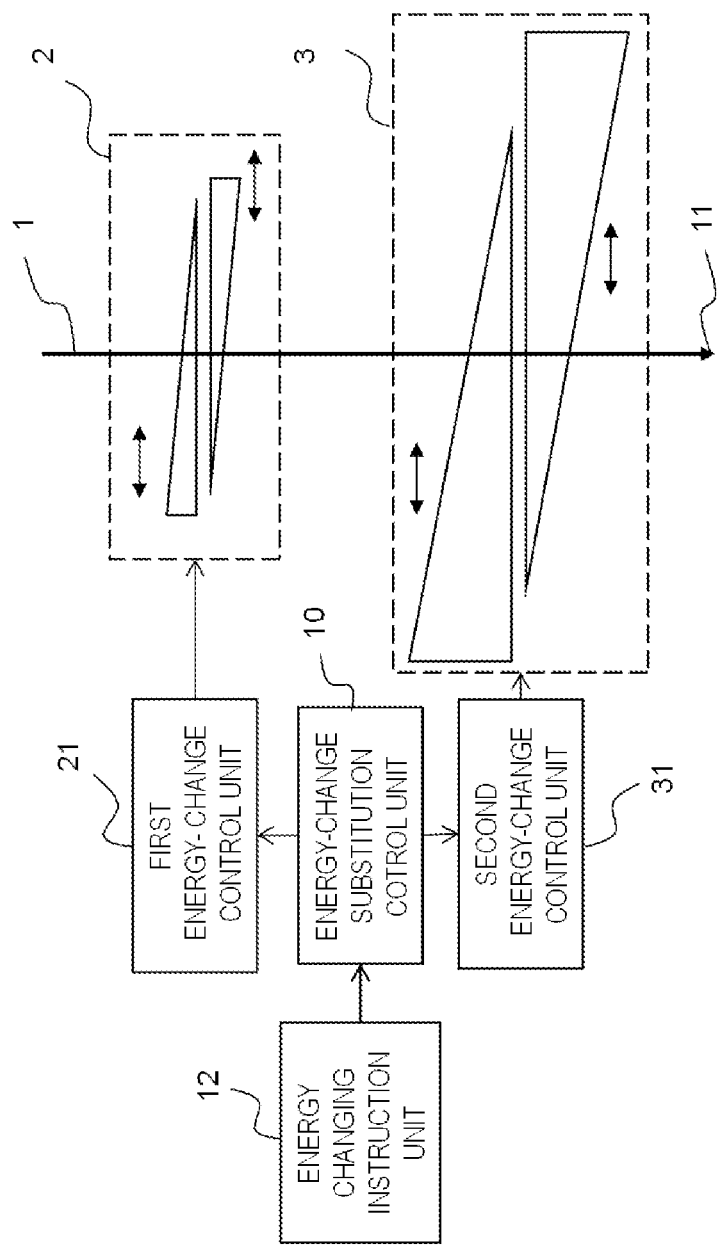
FIG. 1 is a block diagram showing a configuration of a particle-beam energy changing apparatus according to Embodiment 1 of the present invention.

FIG. 1 is a block diagram showing a configuration of a particle-beam energy changing apparatus according to Embodiment 1 of the present invention. Referring to FIG. 1, designated at 1 is a particle beam that is extracted from a particle beam accelerator (not shown) and has a predetermined particle energy; at 2, a first energy changing unit; at 3, a second energy changing unit; at 21, a first energy-change control unit for controlling the first energy changing unit 2; and at 31, a second energy-change control unit for controlling the second energy changing unit 3. Further, designated at 10 is an energy-change substitution control unit for outputting an instruction to the first energy changing unit 2 and the second energy changing unit 3. The energy-change substitution control unit 10 outputs instructions to the first energy-change control unit 21 and the second energy-change control unit 31 in accordance with a signal from an energy changing instruction unit 12.

The first energy changing unit 2 is configured with two wedge shaped blocks. Varying relative positions of the two wedge blocks changes a total thickness thereof at a position through which the particle beam 1 passes, whereby an energy attenuation amount of the passing particle beam can be changed. The second energy changing unit 3 has a similar configuration. It should be noted that the second energy changing unit 3, since it has wedges thicker and longer than the first energy changing unit 2, is capable of changing the particle beam energy by a larger amount than the first energy changing unit 2.

The wedges of the first energy changing unit 2 and those of the second energy changing unit 3 are actuated by a device, such as called a pneumatic cylinder, a hydraulic cylinder or an electromagnetic actuator, to be moved at respective positions necessary to impart a designated energy attenuation to the passing particle beam. For actuating these wedges, other means may be employed. Mass of the wedges of the first energy changing unit 2 is smaller than that of the wedges of the second energy changing unit 3. Accordingly, the maximum speed for varying the thickness of the first energy changing unit 2 is faster than the maximum speed for varying the thickness of the second energy changing unit 3, so that the first energy changing unit 2 can change its attenuation amount more quickly than the second energy changing unit 3.

A particle beam 11 after passing through the first energy changing unit 2 and the second energy changing unit 3 has a changed energy level and travels toward an irradiation subject. FIG. 1 shows a configuration in which the particle beam passes in the following order: the beam passes first through the first energy changing unit 2 having smaller maximum energy-attenuation capability and then passes through the second energy changing unit 3 having larger maximum energy-attenuation capability than that of the first energy changing unit 2. However, the beam may be passed in reverse order.

Figure 2:
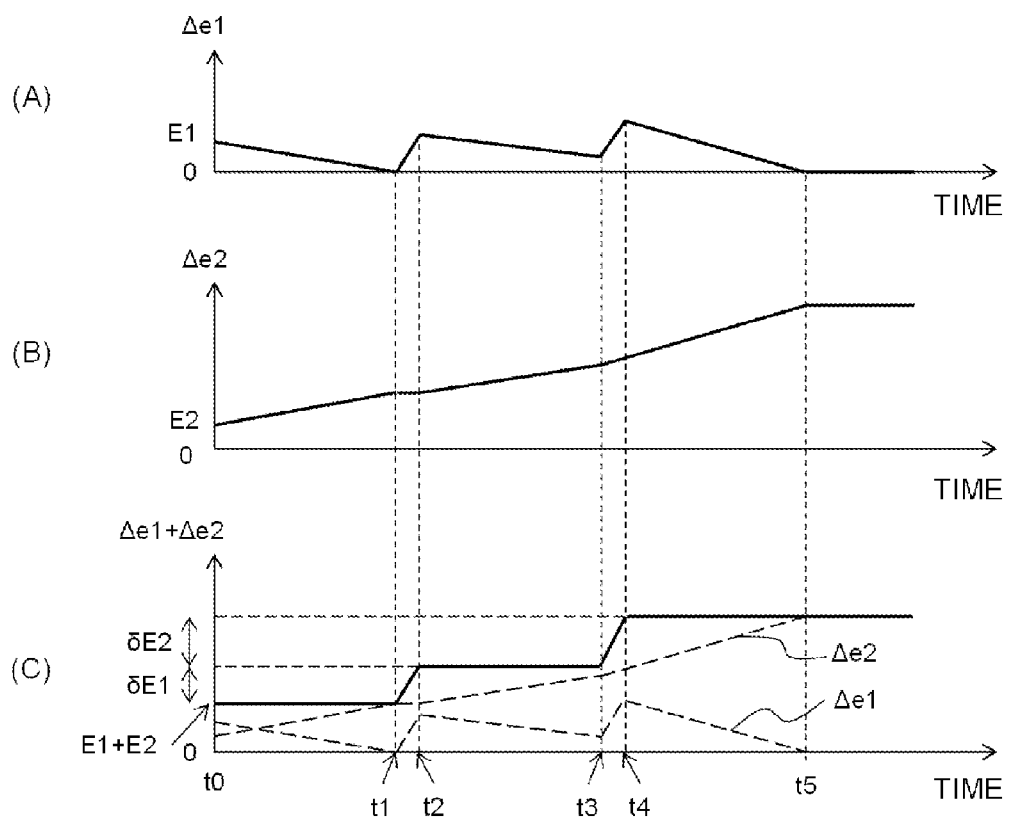
FIG. 2 is a diagram for explaining an operation of the particle-beam energy changing apparatus according to Embodiment 1 of the present invention.

Next, an operation of the particle-beam energy changing apparatus according to Embodiment 1 of the present invention will be described with reference to FIG. 1 and FIG. 2. FIGS. 2A through 2C are diagrams showing time variations of an energy attenuation amount $\Delta e_1$ that the first energy changing unit 2 imparts to the particle beam, an energy attenuation amount $\Delta e_2$ that the second energy changing unit 3 imparts to the particle beam, and the summation of energy attenuation amounts $\Delta e_1 + \Delta e_2$ that the first energy changing unit 2 and the second energy changing unit 3 impart to the particle beam, respectively. In FIG. 2C, the attenuation amount $\Delta e_1$ by the first energy changing unit 2 and the attenuation amount $\Delta e_2$ by the second energy changing unit 3 are also shown in broken lines.

The particle beam 1 having an energy $E_0$ is extracted from a not-shown particle beam accelerator or the like, and passes first through the first changing unit 2 and then passes through the second energy changing unit 3. The total attenuation amount $\Delta e_1 + \Delta e_2$, which the particle beam 1 is subject to after passing through the second energy changing unit 3, is proportional to total path thickness of the first energy changing unit 2 and the second energy changing unit 3. The energy of the particle beam 11 after passing becomes $E_0 - \Delta e_1 - \Delta e_2$. As shown in FIG. 2, it is assumed that at a time $t_0$, an attenuation amount by the first energy changing unit 2 is $E_1$ and an attenuation amount by the second energy changing unit 3 is $E_2$. At this time, the energy of the particle beam 11 after passing through the second energy changing unit 3 becomes $E_0 - E_1 - E_2$. After that, in accordance with an instruction of the energy-change substitution control unit 10, the first energy-change control unit 21 controls the first energy changing unit 2 to decrease its attenuation amount and at the same time the second energy-change control unit 31 controls the second energy changing unit 3 to increase its attenuation amount. During this control period from the time $t_0$ to a time $t_1$, the thicknesses of the first energy changing unit 2 and the second energy changing unit 3 are controlled to vary so that the summation of attenuation amounts by the first energy changing unit 2 and the second energy changing unit 3 is kept always constant, i.e., $\Delta e_1 + \Delta e_2 = E_1 + E_2$. In this case, the attenuation amount by the first energy changing unit 2 is controlled so as to decrease to zero at the time $t_1$. Put differently, during the period from the time $t_0$ to the time $t_1$, a substitution control is performed in such a manner that the attenuation amount by the second energy changing unit 3 is substituted for that by the first energy changing unit 2.

Upon finishing the particle beam irradiation under this condition, the energy-change substitution control unit 10 outputs to the first energy-change control unit 21 an energy changing instruction to quickly move the wedge positions of the first energy changing unit 2. This brings a designated change in thickness thereof in a short period from the time $t_1$ to a time $t_2$, so that energy attenuation amount by the first energy changing unit 2 is changed by $\delta E_1$. At the time $t_2$, the particle beam 11 after passing through the first energy changing unit 2 and the second energy changing unit 3 reduces its energy to $E_0 - E_1 - E_2 - \delta E_1$. Then, the irradiation subject (not shown) is irradiated with a designated number of particles of the particle beam 11 having this energy level. This irradiation period continues as long as about one second in some cases of particle beam therapy. During the period from the time $t_1$ to the time $t_2$, the attenuation amount by the second energy changing unit 3 may be unchanged or changed. In either case, it is adequate as long as the total attenuation amount by the first energy changing unit 2 and the second energy changing unit 3 at the time $t_2$ are changed to become large by $\delta E_1$ from the total attenuation amount at the time $t_1$. In other words, when controlling change of the particle beam energy, a control is performed such that particle beam energy is changed by varying at least the attenuation amount by the first energy changing unit 2 that is capable of changing its attenuation amount quickly.

While the irradiation is performed under the energy condition $E_0-E_1-E_2-\delta E_1$, i.e., during a period from the time $t_2$ to a time $t_3$, the energy-change substitution control unit 10 controls the first energy-change control unit 21 and the second energy-change control unit 31, i.e., performs the substitution control in such a manner that decrease the attenuation amount $\Delta e_1$ by the first energy changing unit 2 and, at the same time, to increase the attenuation amount $\Delta e_2$ by the second energy changing unit 3. During this substitution control, the first energy changing unit 2 and the second energy changing unit 3 are controlled to keep the total attenuation amount at $E_1+E_2+\delta E_1$. As shown in FIG. 2A, the energy attenuation amount by first energy changing unit 2 may not necessarily be zero at the time $t_3$, but it is adequate as long as the total attenuation amount is $\Delta e_1+\Delta e_2=E_1+E_2+\delta E_1$ at the time $t_3$.

Upon finishing the irradiation with the energy $E_0-E_1-E_2-\delta E_1$, the energy changing instruction unit 12 outputs an instruction to change the energy, and then a subsequent irradiation is performed with the beam energy being further decreased, for example, by $\delta E_2$. At this time, the first energy changing unit 2 is moved quickly as before so that the attenuation amount thereby increases by $\delta E_2$ at a time $t_4$. Since the attenuation amount by the first energy changing unit 2 is changed to not zero at the time $t_3$ (the attenuation amount at this time is expressed by $E_3$, for example), the attenuation amount by the first energy changing unit 2 is changed to $\delta E_2+E_3$ larger than $\delta E_2$. In this case, the maximum attenuation amount by the first energy changing unit 2 needs to be larger than $\delta E_2+E_3$. Hence, the attenuation amount by the first energy changing unit 2 may not be zero at the time $t_3$, as described above. The particle beam energy is thus changed to $E_0-E_1-E_2-\delta E_1-\delta E_2$ at the time $t_4$, and an irradiation with this energy can be immediately started. Then, while the irradiation is performed with this energy, the attenuation amount by the first energy changing unit 2 is decreased and the attenuation amount by the second energy changing unit 3 is increased as before, so that the particle beam energy is controlled to be kept constant at $E_0-E_1-E_2-\delta E_1-\delta E_2$ during this period.

After the substitution control finishes and the attenuation amount by the second energy changing unit 3 is changed to $E_1+E_2+\delta E_1+\delta E_2$ at a time $t_5$, the irradiation with the particle beam energy of $E_0-E_1-E_2-\delta E_1-\delta E_2$ may be continued using the attenuation by the second energy changing unit 3 alone, as shown in FIG. 2. In this way, the control is performed such that the attenuation amount by the second energy changing unit 3 is substituted for all of or part of the attenuation amount by the first energy changing unit 2 in a period shorter than that of a constant energy irradiation. Thereafter, when changing energy of the particle beam, the particle-beam energy change is performed by primarily changing the attenuation amount by the first energy changing unit 2 having smaller maximum energy-attenuation capability and able to being actuated quickly. Note that when changing energy of the particle beam, the attenuation amount by the second energy changing unit 3 may be either unchanged or changed. For example, in FIG. 2, it is adequate as long as $\Delta e_1+\Delta e_2$ at the time $t_2$ or the time $t_4$ is changed to a designated attenuation amount after energy change.

Figure 3:
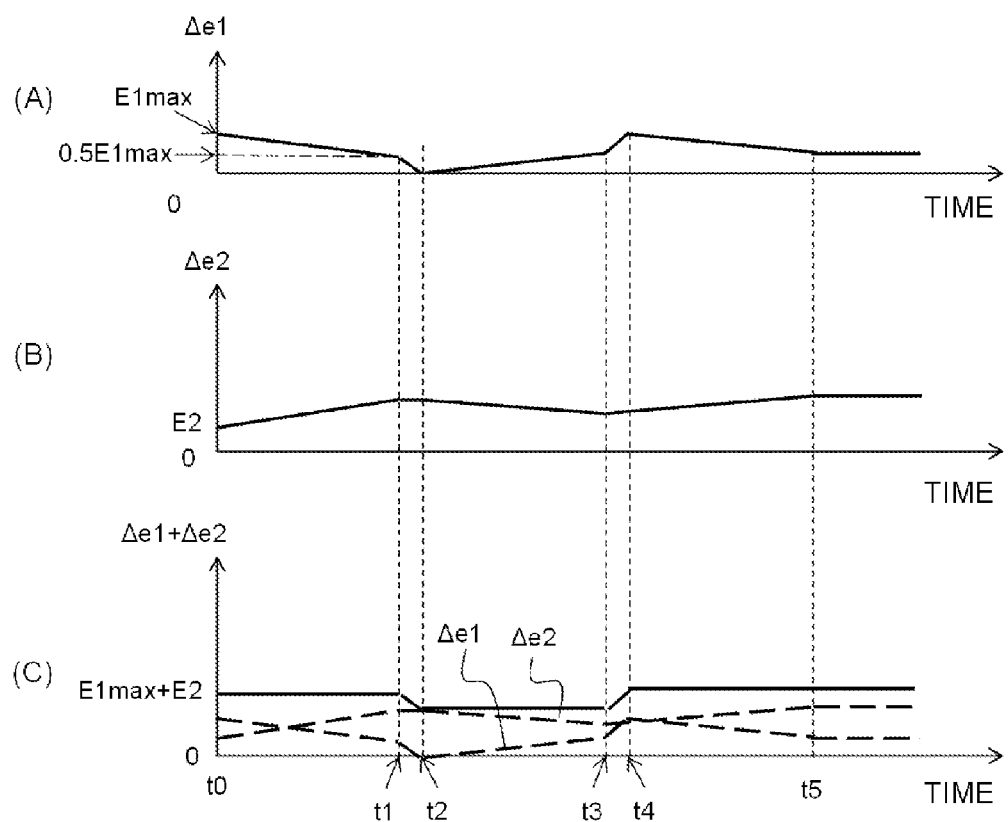
FIG. 3 is a diagram for explaining another operation of the particle-beam energy changing apparatus according to Embodiment 1 of the present invention.

FIG. 3 is a diagram different from FIG. 2, showing another operation of the particle-beam energy changing apparatus. FIGS. 3A through 3C are diagrams showing time variations of an attenuation amount $\Delta e_1$ that the first energy changing unit 2 imparts to the particle beam, an attenuation amount $\Delta e_2$ that the second energy changing unit 3 imparts to the particle beam, and the summation of attenuation amounts $\Delta e_1+\Delta e_2$ that the first energy changing unit 2 and the second energy changing unit 3 impart to the particle beam, respectively. By the operation shown in FIG. 2, the attenuation amount by the particle-beam energy changing apparatus cannot be decreased quickly, i.e., energy of the particle beam cannot be increased quickly. As shown in FIG. 3, the attenuation amount $\Delta e_1$ by the first energy changing unit 2 for a single change is performed within half the maximum attenuation amount by the first energy changing unit 2, thereby allowing the particle beam energy to be increased or decreased quickly. During a period from a time $t_0$, at which the attenuation amount $\Delta e_1$ by the first energy changing unit 2 is its maximum value $E_{1max}$, to a time $t_1$, the attenuation amount $\Delta e_1$ by the first energy changing unit 2 is changed from $E_{1max}$ to $0.5E_{1max}$. During that period, the attenuation amount $\Delta e_2$ by the second energy changing unit 3 is increased so as to keep the relation of $\Delta e_1+\Delta e_2=E_{1max}+E_2$. Then, by decreasing the attenuation amount by the first energy changing unit 2 to zero during a short period from the time $t_1$ to a time $t_2$, the total attenuation amount of the attenuation amount $\Delta e_1$ by the first energy changing unit 2 and the attenuation amount $\Delta e_2$ by the second energy changing unit 3 can be decreased to $0.5E_{1max}+E_2$, i.e., the particle beam energy can be increased by $0.5E_{1max}$.

Next, during the period from the time $t_2$ to a time $t_3$, the attenuation amount by the first energy changing unit 2 is increased to $0.5E_{1max}$. During that period, the attenuation amount $\Delta e_2$ by the second energy changing unit 3 is decreases so as to keep the relation of $\Delta e_1+\Delta e_2=0.5E_{1max}+E_2$. Then, by increasing the attenuation amount by the first energy changing unit 2 to less than its maximum value, for example, $0.9E_{1max}$ during a short period from the time $t_3$ to a time $t_4$, the total attenuation amount by the first energy changing unit 2 and the second energy changing unit 3 can be increased to $0.9E_{1max}+E_2$, i.e., the particle beam energy can be decreased by $0.4E_{1max}$. Afterward, while keeping constant the total attenuation amount at $\Delta e_1+\Delta e_2=0.9E_{1max}+E_2$ during a period from the time $t_4$ to a time $t_5$, the attenuation amounts by the first energy changing unit 2 and the second energy changing unit 3 are controlled so that the attenuation amount by the first energy changing unit 2 is changed to $0.5E_{1max}$ at time $t_5$.

In this way, by changing the attenuation amount by the first energy changing unit 2 centering around half of its maximum attenuation amount, the particle beam energy can be quickly increased or decreased within a limit of half the maximum attenuation amount by the first energy changing unit 2. In other words, it is desired that the attenuation amount by the first energy changing unit 2 be half of its maximum attenuation amount at a start of changing the particle beam energy quickly. Note that depending on a particle-beam energy changing pattern, the attenuation amount by the first energy changing unit 2 is not changed centering around half the maximum attenuation amount thereby, but may be determined taking into account an energy difference to be changed subsequently.

As has been described above, in a particle-beam energy changing apparatus according to Embodiment 1, since the maximum attenuation amount by the first energy changing unit 2 is set smaller than the maximum attenuation amount by the second energy changing unit 3, particle beam irradiation with quick energy change of the particle beam can be performed without actuating quickly the second energy changing unit 3 unsuitable for quick actuation owing to its relatively large mass. The elimination of the need for actuating quickly the large-mass second energy changing unit 3 suppresses quick mechanical actuation, thereby allowing the energy change to be performed silently as well as the total irradiation time to be reduced. Furthermore, when energy of the particle beam after passing through the particle-beam energy changing apparatus is controlled to be constant, a substitution control is performed in such a manner that the attenuation amounts by the first energy changing unit 2 and the second energy changing unit 3 is substituted for each other. Therefore, the particle beam energy can be changed more quickly when changing the energy.

Embodiment 2

Figure 4:
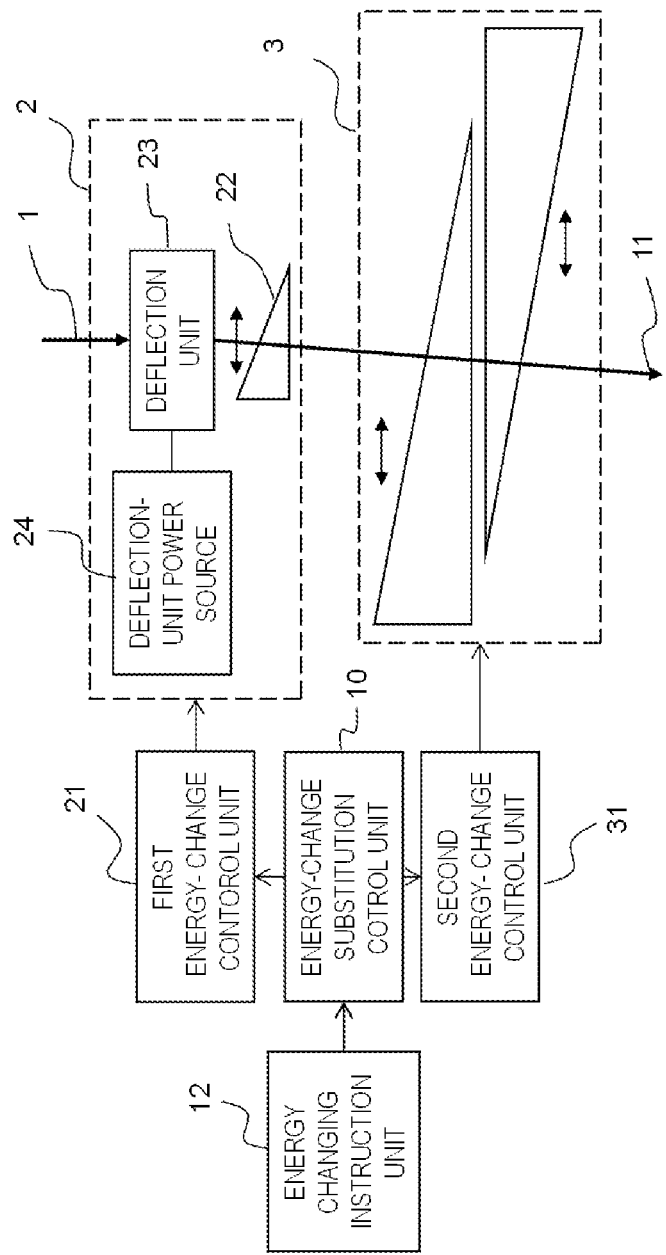
FIG. 4 is a block diagram showing a configuration of a particle-beam energy changing apparatus according to Embodiment 2 of the present invention.

FIG. 4 is a block diagram showing a configuration of a particle-beam energy changing apparatus according to Embodiment 2 of the present invention. In FIG. 4, the same reference numerals as those in FIG. 1 denote the same or equivalent components. Referring to FIG. 4, a deflection unit 23 includes an electromagnet that is driven by a deflection-unit power source 24 to vary the traveling direction of the entering particle beam 1. Deflecting the particle beam 1 from its traveling direction by the deflection unit 23 varies the passing position of the particle beam through an energy attenuation element 22 that has a thickness varying part like a wedge shaped block. The particle-beam energy changing apparatus is thus configured to change an energy attenuation amount to be imparted to the particle beam 1.

In the particle-beam energy changing apparatus according to Embodiment 2, its basic operation of changing the attenuation amount is the same as that of the particle-beam energy changing apparatus according to Embodiment 1 described above. A difference is that a first energy changing unit 2 includes the deflection unit 23, the deflection-unit power source 24, and the energy attenuation element 22. The deflection-unit power source 24 changes a magnetic excitation amount of the deflection unit 23 by receiving an energy changing instruction from the energy changing instruction unit 12, whereby the path of the particle beam 1 is shifted and the passing position of the particle-beam through the energy attenuation element 22 is changed, thus changing the energy attenuation amount quickly. After that, a particle beam irradiation is started with the changed energy. During the irradiation, the second energy changing unit 3 is controlled to increase its thickness by the second energy-change control unit 31, while the particle beam 1 is controlled to pass through a thinner portion of the energy attenuation element 22 by changing the magnetic excitation amount of the deflection unit 23 in accordance with an instruction of the first energy-change control unit 21. During that period, in accordance with an instruction from the energy-change substitution control unit 10, the total attenuation amount by the first energy changing unit 2 and the second energy changing unit 3 is controlled to be constant. In this way, the attenuation amount by the second energy changing unit 3 is substituted for that by the first energy changing unit 2 during the constant energy irradiation.

Since the first energy changing unit 2 includes the deflection unit 23 and the energy attenuation element 22 having the sloping thickness, a new advantageous effect by Embodiment 2 is that the energy attenuation amount by the first energy changing unit 2 can be changed quickly by an electromagnetic operation alone without need of mechanical actuation. As a result, particle beam irradiation can be performed with more quick change of the particle beam energy. Moreover, eliminating a quick mechanical control of the first energy changing unit 2 further reduces noise and enhances reliability as well.

Embodiment 3

Figure 5:
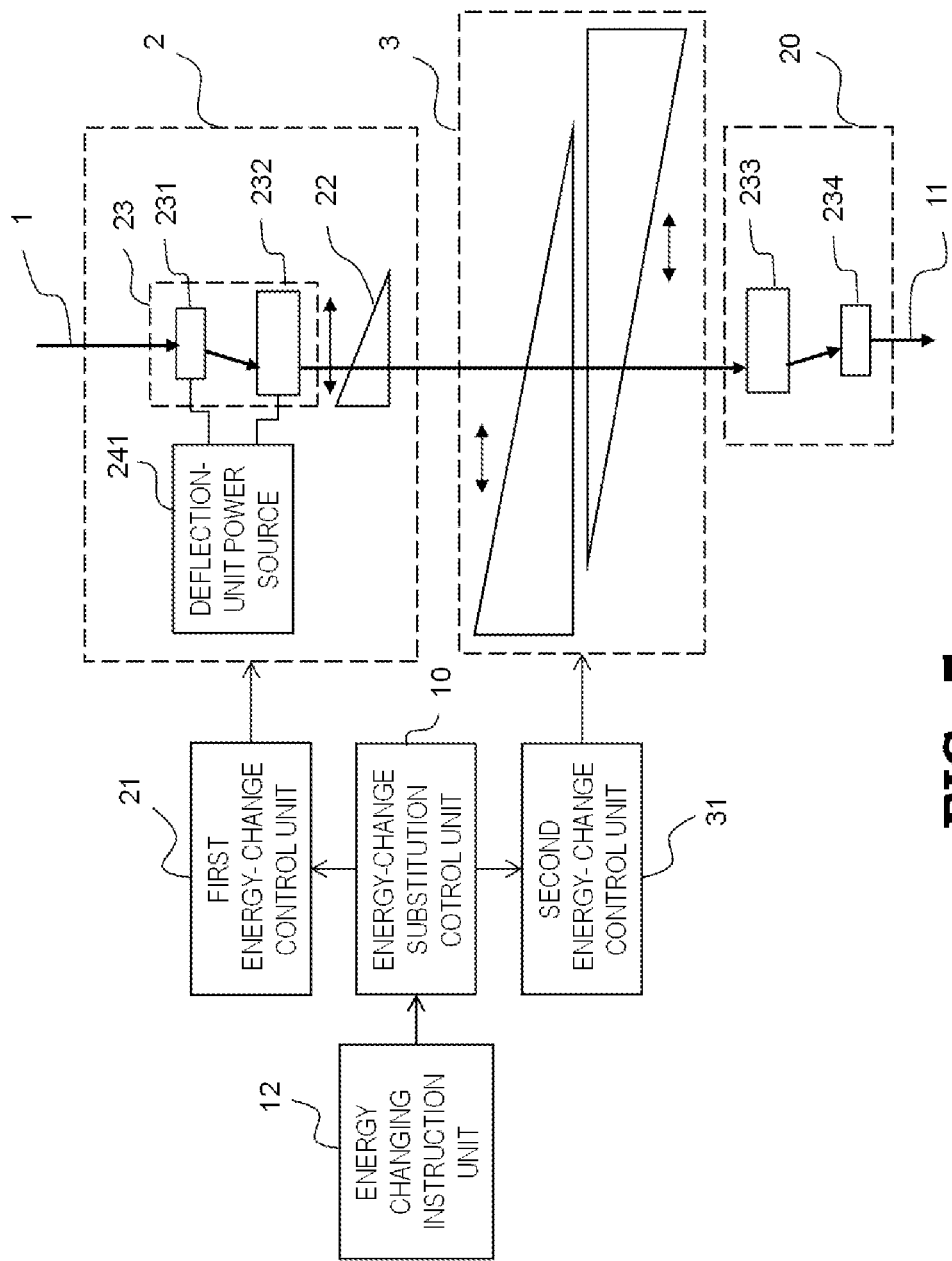
FIG. 5 is a block diagram showing a configuration of a particle-beam energy changing apparatus according to Embodiment 3 of the present invention.

FIG. 5 is a block diagram showing a configuration of a particle-beam energy changing apparatus according to Embodiment 3 of the present invention. In FIG. 5, the same reference numerals as those in FIGS. 1 and 4 denote the same or equivalent components. Embodiment 3 is different compared to Embodiment 2 in that a deflection unit 23 is configured to shift the path of the particle beam in parallel. That is, the particle beam 1 entered into a first deflector 231 is deflected from its traveling direction. After that, the path of particle beam is restored by a second deflector 232 to a path that is parallel with the traveling direction of the particle beam entering into the deflection unit 23. A deflection-unit power source 241 controls the first deflector 231 and the second deflector 232 on the basis of an instruction from the first energy-change control unit 21 so that the particle beam 1 passes through a designated thickness portion of the energy attenuation element 22. The particle beam shifted parallel from the original path passes through the energy attenuation element 22 and then through the second energy changing unit 3. After that, a path-restoring deflection unit 20, which includes a first path-restoring deflector 233 and a second path-restoring deflector 234, corrects the path in a manner opposite to the deflection unit 23, to restores the path of a particle beam 11 to be extracted from the path-restoring deflection unit 20 in line with the path of the particle beam 1 entering into the first energy changing unit 2.

New advantageous effects by Embodiment 3 are as follows. Since the particle beam energy alone can be changed quickly while keeping the particle beam always at the same traveling angle, the energy can be changed with high accuracy. Moreover, since the path of the particle beam 11 extracted from the particle-beam energy changing apparatus does not shifted, lowering of irradiation accuracy can be prevented.

In Embodiment 3 shown in FIG. 5, it should be noted that the energy attenuation element 22 and the deflection unit 23, which are constituent members of the first energy changing unit 2, are preferably arranged in such positions that make small the correlation coefficient (represented as $\eta$ in the field of particle beam accelerators) between the particle beam energy and its path in the particle beam transport system. With this arrangement, even if energy of the particle beam 1 entering into the first energy changing unit 2 fluctuates slightly, the entering path of the particle beam 1 does not deviate largely, so that the position of the particle beam after shifted is determined only by the control to the deflection unit 23. Hence, the particle beam enters into the energy attenuation element 22 at the position in accordance with the instruction. As a result, even if energy of the particle beam 1 fluctuates slightly, the first energy changing unit 2 can be change the energy of the particle beam 1 as expected. Thus, the energy change can be performed with higher accuracy.

Embodiment 4

Figure 6:
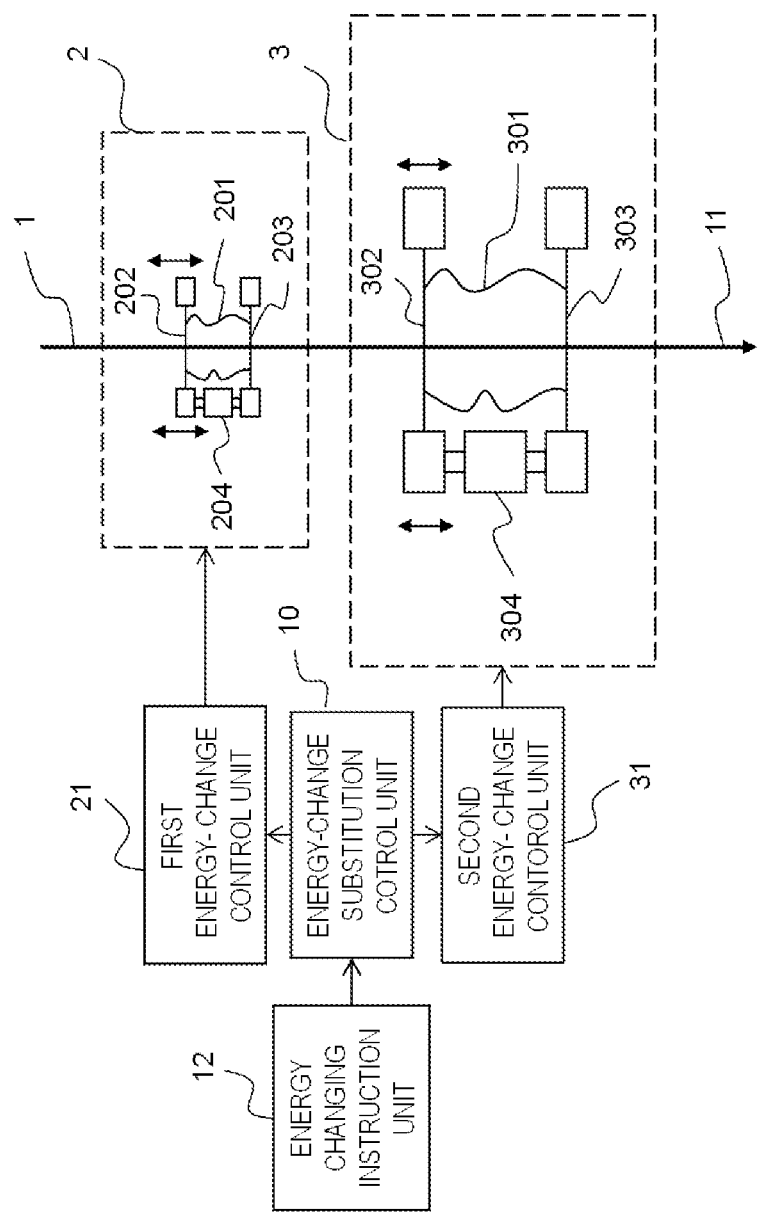
FIG. 6 is a block diagram showing a configuration of a particle-beam energy changing apparatus according to Embodiment 4 of the present invention.

FIG. 6 is a block diagram showing a configuration of a particle-beam energy changing apparatus according to Embodiment 4 of the present invention. In FIG. 6, the same reference numerals as those in FIGS. 1, 4 and 5 denote the same or equivalent components. Embodiment 4 is an embodiment in which a liquid such as water is used as an attenuator of an energy changing unit. A first energy changing unit 2 includes a container 201 for storing a liquid such as water and particle beam pass-through plates 202 and 203 provided on the top and bottom of the container. The space enclosed by the container 201 and the pass-through plates 202 and 203 is filled with a particle-beam attenuating liquid such as water. Here, the container 201 is formed of a flexible material. A liquid thickness adjuster 204 varies the distance between the pass-through plates 202 and 203, whereby thickness of the portion that the particle beam passes through is varied, thus changing the attenuation amount to be imparted to the particle beam. Likewise, a second energy changing unit 3 includes a container 301 for storing a liquid such as water and particle beam pass-through plates 302 and 303 provided on the top and bottom of the container. The distance between the pass-through plates 302 and 303 is varied by a liquid thickness adjuster 304.

An attenuation amount changing operation of the energy changing apparatus according to Embodiment 4 is basically the same as Embodiment 1. A difference is that change of the attenuation amounts by the first energy changing unit 2 and the second energy changing unit 3 is achieved not by movement of the wedges but by variation in thickness of the liquid. The maximum height of the container 201 for the first energy changing unit 2 is lower than that of the container 301 for the second energy changing unit 3, i.e., the maximum attenuation amount by the first energy changing unit 2 is smaller than that by second energy changing unit 3. Accordingly, the first energy changing unit 2 is able to change quickly its beam pass length.

A new advantageous effect by Embodiment 4 is that the energy changing units can be configured more compact than using the wedge plates. In the above, varying the distances between the pass-through plates 202, 203 and between the pass-through plates 302, 303 causes the liquid energy-attenuator to vary in its thickness. Apart from this, a rubber-like elastic container filled with a liquid such as water can vary thickness of the portion that the particle beam passes through by varying thickness of the filled liquid by varying pressure. This also brings about the same effect as the above.

Embodiment 5

Figure 7:
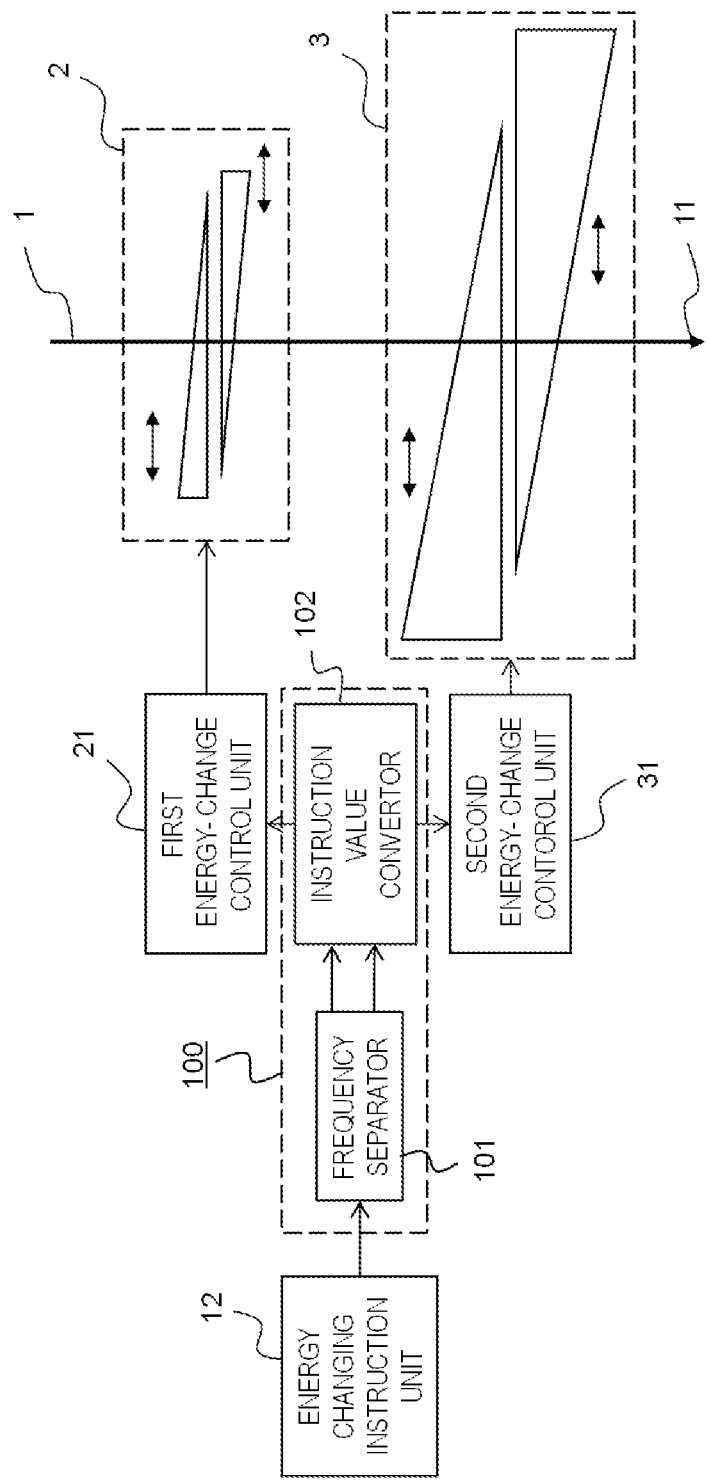
FIG. 7 is a block diagram showing a configuration of a particle-beam energy changing apparatus according to Embodiment 5 of the present invention.

FIG. 7 is a block diagram showing a configuration of a particle-beam energy changing apparatus according to Embodiment 5 of the present invention. Embodiment 5 is an embodiment in which instruction values for the first and the second energy-change control units 21, 31 are generated. The energy changing instruction unit 12 sends to an energy-change substitution control unit 100 data indicating, for example, time variation of energy attenuation amount to be imparted to the particle beam 1. The energy-change substitution control unit 100 includes a frequency separator 101 and an instruction value converter 102.

Figure 8:
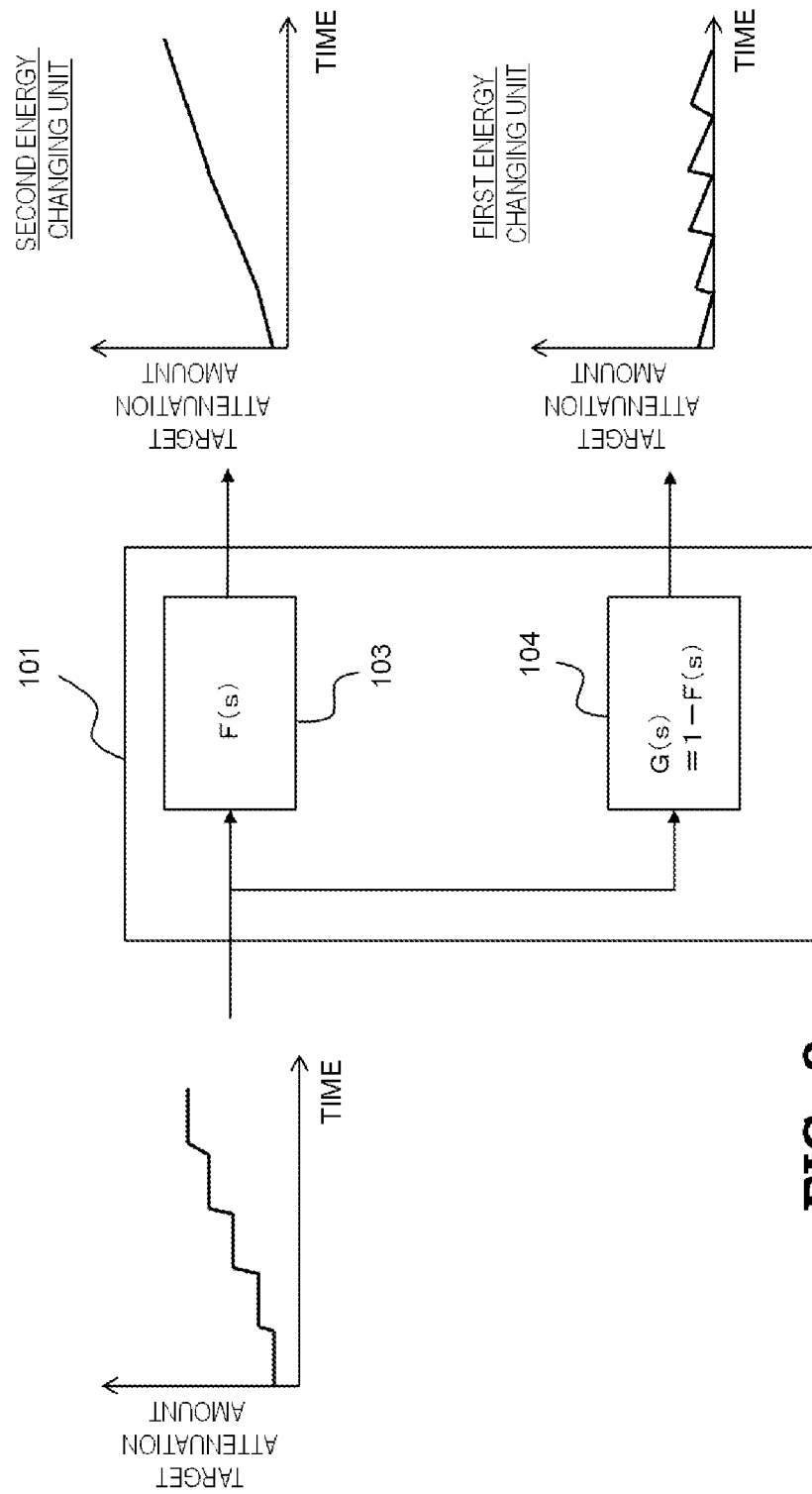
FIG. 8 shows diagrams illustrating a configuration and an operation of a frequency separator of the particle-beam energy changing apparatus according to Embodiment 5 of the present invention.

A block diagram of the frequency separator 101 according to Embodiment 5 is shown in FIG. 8. Target values of energy attenuation amounts sent from the energy changing instruction unit 12 are data including temporal target attenuation amounts arranged in time-series order. That is, the target attenuation-amount values are given as a time-series signal shown in the left side of FIG. 8, for example. These target attenuation-amount values represent a case of repeating irradiation operations in which a continuous irradiation is performed with a designated energy for a certain period of time and then another continuous irradiation is subsequently performed with a changed energy. In order to obtain attenuation-amount instruction values for the first energy changing unit 2 and the second energy changing unit 3 in terms of the target attenuation-amount values, the following operation is performed taking into account the characteristics of the first energy changing unit 2 and the second energy changing unit 3.

The target attenuation-amount value signal shown in left side of FIG. 8, which is an input to the frequency separator 101, is separated into a signal for the first energy changing unit 2 and that for the second energy changing unit 3 using filters. Since the first energy changing unit 2 is compact and actuated quickly, it has a high-frequency response characteristic. Hence, it is adapted to be responsible for higher frequency components of the target attenuation-amount value signal. On the other hand, since the second energy changing unit 3 is large size and its energy changing range is wide, it has a low-frequency response characteristic. Hence, it is adapted to be responsible for lower frequency components thereof. FIG. 8 shows that the target attenuation-amount value signal is separated using the filters. Accordingly, the filters used here are complementary (F(s)+G(s)=1) as shown in FIG. 8. Note that the total target attenuation amount achieved by the first energy changing unit 2 and the second energy changing unit 3 should be in accordance with an original therapy plan.

In FIG. 8, F(s) is a low pass filter 103 for the second energy changing unit 3 and G(s) (=1−F(s)) is a high pass filter 104 for the first energy changing unit 2. Target attenuation-amount value signals separated by these filters are the two signals shown in the right side of FIG. 8. Note that, providing no high pass filter but the low pass filter 103 alone, the higher frequency components may be obtained, using a computing unit, by subtracting the lower frequency component signal separated by the low pass filter 103 from the input signal, i.e., the target attenuation-amount value signal. Conversely, providing no low-pass filter but the high-pass filter, the lower frequency components may be obtained by subtracting the higher frequency component signal separated by the high pass filter from the input signal, i.e., the target attenuation-amount value signal.

The instruction value converter 102 outputs instruction values of attenuation amounts by the respective energy changing units, which are converted from the respective target attenuation-amount values so that the instruction values correspond to the actuation means of the respective energy changing units, to control the first energy changing unit 2 and the second energy changing unit 3. With the above configuration, signals for controlling the first energy changing unit 2 and the second energy changing unit 3 can be automatically generated from time series variation data of target attenuation amount values sent from the energy changing instruction unit 12. Accordingly, the configuration becomes simplified.

Embodiment 6

Figure 9:
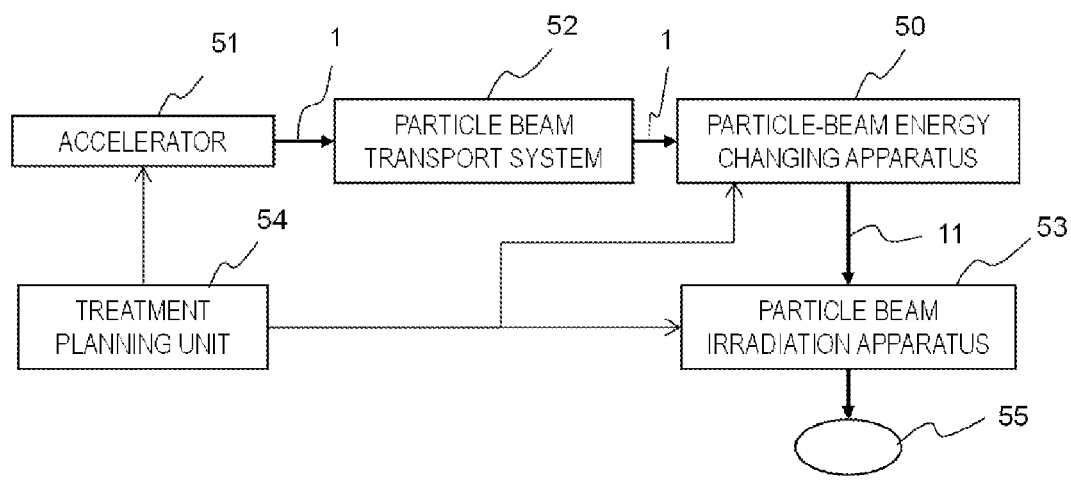
FIG. 9 is a block diagram showing a configuration of a particle beam therapy system according to Embodiment 6 using a particle-beam energy changing apparatus of the present invention.

FIG. 9 is a block diagram showing a configuration of a particle beam therapy system using a particle-beam energy changing apparatus of the present invention. The particle beam 1 extracted from an accelerator 51 travels through a particle beam transport system 52, and then its energy is changed by a particle-beam energy changing apparatus 50. An irradiation subject 55 is irradiated with the particle beam 11 having the changed energy level. Here, the irradiated subject 55 is a diseased site of human body, such as a tumor. The accelerator 51, the particle-beam energy changing apparatus 50, a particle beam irradiation apparatus 53, and the like are controlled in accordance with instructions from a treatment planning unit 54, to form dose distribution of the particle beam in a three-dimensional region in accordance with the shape of the diseased site.

Changing particle beam energy with which the irradiation subject 55 is irradiated causes change in Bragg peak position. Accordingly, dose distribution can be formed in a three-dimensional region in accordance with a therapy plan by irradiating the irradiation subject 55 with a particle beam of changing energy. This energy change is implemented by an energy changing operation of the particle-beam energy changing apparatus 50. Specifically, the irradiation subject 55 is irradiated with the particle beam whose energy is changed by using any of the particle-beam energy changing apparatus of Embodiments 1 through 5. Use of the particle-beam energy changing apparatus according to the present invention enables the particle beam to be changed quickly and with low noise, therefore providing a particle beam therapy system that performs irradiation silently in a short time.

Embodiment 7

In particle beam therapy systems and the like, a target may move periodically accompanied by respiratory motion during irradiation. In this case, in order to irradiate accurately the target with the particle beam at a designated irradiation position scheduled in a therapy plan, the irradiation is sometimes implemented with a particle beam whose energy is corrected by being shifted slightly from a planned energy level. Since there is a periodic recurrence of respiratory motion within a certain period of time, modulation of the particle beam energy synchronously with the periodic respiratory motion allows the particle beam irradiation at a designated position in a diseased site in accordance with the therapy plan. In Embodiment 7, in addition to the substitution controls described in Embodiments 1 through 5, the first energy changing unit 2 that is actuatable more quickly is controlled to superimpose an attenuation amount change for correcting the beam energy synchronously with the above-described periodic motion. This brings about an effect of enabling accurate particle-beam irradiation in accordance with the therapy plan even when a diseased site has a periodic fluctuation in its position.

In some cases, the particle beam may have predictable fluctuation in its own energy. An example of the predictable fluctuation is, for example, a periodical energy fluctuation of the particle beam extracted from the accelerator. In addition to the substitution controls described in Embodiments 1 through 5, the first energy changing unit 2 that is actuatable more quickly is controlled to superimpose an attenuation amount change that corrects the above-described predictable energy fluctuation so as to reduce the energy fluctuation. This allows irradiation of a diseased site with the particle beam in accordance with a therapy plan without being affected by the predictable energy fluctuation of the particle beam. As a result, an effect is brought about that can perform irradiation with higher accuracy.

As described above, when the particle beam energy needs to be corrected, the correction is performed by the first energy changing unit 2 that is capable of changing its attenuation amount more quickly, thereby enabling the irradiation with high accuracy.

Reference Numerals

1: particle beam
2: first energy changing unit
3: second energy changing unit
10, 100: energy-change substitution control unit
11: particle beam after its energy is altered
12: energy changing instruction unit
101: frequency separator

The invention claimed is:

1. A particle-beam energy changing apparatus comprising:
a first energy changing unit and a second energy changing unit each having a particle-beam energy attenuator and arranged so that a particle beam passes through the first energy changing unit and the second energy changing unit, to change energy of the passing particle beam by varying thicknesses of the attenuators; and
an energy-change substitution control unit which controls the first energy changing unit and the second energy changing unit,
wherein a maximum attenuation amount by the first energy changing unit is set smaller than a maximum attenuation amount by the second energy changing unit, and
the energy-change substitution control unit is configured to perform a control of changing energy of the particle beam at least by changing an attenuation amount by the first energy changing unit when energy of the particle beam is controlled to change, and
a substitution control that substitutes an attenuation amount by the first energy changing unit and an attenuation amount by the second energy changing unit for each other by changing the attenuation amount by the first energy changing unit and the attenuation amount by the second energy changing unit so that a total attenuation amount of the attenuation amount by the first energy changing unit and the attenuation amount by the second energy changing unit remains unchanged when energy of the particle beam after passing through the particle-beam energy changing apparatus is controlled to be constant.

2. The particle-beam energy changing apparatus according to claim 1, wherein a maximum speed of changing an attenuation amount by the first energy changing unit is faster than a maximum speed of changing an attenuation amount by the second energy changing unit.

3. The particle-beam energy changing apparatus according to claim 1, wherein values of target attenuation amounts to be imparted to the particle beam are given as time series data of the target attenuation-amount values, and instructions to the first energy changing unit and the second energy changing unit are generated on the basis of two data sets separated in frequency from the time series data of the target attenuation-amount values.

4. The particle-beam energy changing apparatus according to claim 1, wherein correction of energy of the particle beam is performed by varying an attenuation amount by the first energy changing unit.

5. A particle beam therapy system comprising a particle-beam energy changing apparatus according to claim 1.

6. A method of changing energy of a particle beam, in which using a first energy changing unit and a second energy changing unit each having a particle-beam energy attenuator, energy of a particle beam passing through both units is changed by varying thicknesses of the particle-beam energy attenuators, wherein a maximum attenuation amount by the second energy changing unit is set larger than a maximum attenuation amount by the first energy changing unit, the method of changing energy of a particle beam comprising:
changing the particle beam energy at least by changing an attenuation amount by the first energy changing unit when the particle beam energy is controlled to change; and
substituting an attenuation amount by the first energy changing unit and an attenuation amount by the second energy changing unit for each other, when energy of the particle beam after passing through the first energy changing unit and the second energy changing unit is controlled to be constant, by changing the attenuation amount by the first energy changing unit and the attenuation amount by the second energy changing unit so that a total attenuation amount of the attenuation amount by the first energy changing unit and the attenuation amount by the second energy changing unit remains unchanged.

* * * * *